United States Patent
Kim et al.

(10) Patent No.: US 10,338,020 B2
(45) Date of Patent: Jul. 2, 2019

(54) METHOD FOR MEASURING METAL ION PERMEABILITY OF POLYMER FILM AND DEVICE FOR MEASURING METAL ION PERMEABILITY OF POLYMER FILM

(71) Applicant: LG CHEM, LTD., Seoul (KR)

(72) Inventors: Jung Hak Kim, Daejeon (KR); Young Kook Kim, Daejeon (KR); Kwang Joo Lee, Daejeon (KR); Hee Jung Kim, Daejeon (KR); Se Ra Kim, Daejeon (KR); Jung Ho Jo, Daejeon (KR); Seung Hee Nam, Daejeon (KR); Ji Ho Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 3 days.

(21) Appl. No.: 15/529,813

(22) PCT Filed: Jan. 29, 2016

(86) PCT No.: PCT/KR2016/001021
§ 371 (c)(1),
(2) Date: May 25, 2017

(87) PCT Pub. No.: WO2016/122263
PCT Pub. Date: Aug. 4, 2016

(65) Prior Publication Data
US 2017/0328851 A1    Nov. 16, 2017

(30) Foreign Application Priority Data
Jan. 29, 2015  (KR) .................. 10-2015-0014332

(51) Int. Cl.
*G01R 15/08*    (2006.01)
*G01R 27/08*    (2006.01)
(Continued)

(52) U.S. Cl.
CPC ......... *G01N 27/125* (2013.01); *G01N 27/041* (2013.01); *G01N 27/14* (2013.01); *G01N 27/404* (2013.01); *G01N 27/447* (2013.01)

(58) Field of Classification Search
CPC ........ G01R 15/08; G01R 27/08; G01N 27/04; G01N 27/06; G01N 27/12; G01N 27/14; G01N 27/404; G01N 27/62; B23H 5/00
See application file for complete search history.

(56) References Cited

U.S. PATENT DOCUMENTS 4,454,007 A   6/1984  Pace
4,871,427 A   10/1989 Kolesar, Jr.
(Continued)

FOREIGN PATENT DOCUMENTS

CN    86107737 A     6/1987
CN    101246095 A    8/2008
(Continued)

OTHER PUBLICATIONS

Search Report and Written Opinion issued for International Application No. PCT/KR2016/001021 dated Apr. 15, 2016 (18 pages).
(Continued)

*Primary Examiner* — Neel D Shah
(74) *Attorney, Agent, or Firm* — Rothwell, Figg, Ernst & Manbeck, P.C.

(57) ABSTRACT

The present invention relates to a method for measuring metal ion permeability of a polymer film, comprising the steps of: applying a voltage to the polymer film at a temperature of 5° C. to 250° C., while one side of the polymer film is brought into contact with an electrolyte comprising metal ions, an organic solvent and an aqueous solvent; and measuring the change rate of resistance or change rate of current of the polymer film according to time,
(Continued)

after the voltage is applied, and a device for measuring metal ion permeability of a polymer film used therefor.

18 Claims, 3 Drawing Sheets

(51) Int. Cl.
  *B23H 5/00* (2006.01)
  *G01N 27/12* (2006.01)
  *G01N 27/447* (2006.01)
  *G01N 27/04* (2006.01)
  *G01N 27/14* (2006.01)
  *G01N 27/404* (2006.01)

(56) References Cited

U.S. PATENT DOCUMENTS

| | | | |
|---|---|---|---|
| 8,358,137 | B2 | 1/2013 | Uchiyama |
| 8,674,349 | B2 | 3/2014 | Shinoda et al. |
| 8,735,881 | B1 | 5/2014 | Shinoda et al. |
| 2006/0157355 | A1* | 7/2006 | Baskaran ............ C25D 3/02 205/674 |
| 2011/0001500 | A1 | 1/2011 | Uchiyama |
| 2012/0175604 | A1 | 7/2012 | Hanna et al. |
| 2014/0370404 | A1 | 12/2014 | Kato et al. |
| 2017/0038324 | A1 | 2/2017 | Suzumura et al. |
| 2017/0336315 | A1* | 11/2017 | Kim ............ G01N 15/0806 |

FOREIGN PATENT DOCUMENTS

| | | |
|---|---|---|
| CN | 101995430 B | 8/2012 |
| DE | 102005040592 A1 | 3/2007 |
| JP | 03-085440 A | 4/1991 |
| JP | 06-317560 A | 11/1994 |
| JP | H07-130809 A | 5/1995 |
| JP | 2002-156359 A | 5/2002 |
| JP | 2005-009938 A | 1/2005 |
| JP | 2009-081127 A | 4/2009 |
| JP | 4680630 B2 | 5/2011 |
| KR | 10-2000-0006773 A | 2/2000 |
| KR | 20-0258792 Y1 | 12/2001 |
| KR | 20-0288338 Y1 | 9/2002 |
| KR | 10-2010-0038358 A | 4/2010 |
| KR | 10-2010-0041748 A | 4/2010 |
| KR | 10-2012-0081093 A | 7/2012 |
| KR | 10-1311661 B1 | 9/2013 |
| KR | 10-2014-0088889 A | 7/2014 |

OTHER PUBLICATIONS

Burgmayer, P. et al., "An Ion Gate Membrane: Electrochemical Control of Ion Permeability through a Membrane with an Embedded Electrode", Journal of American Chemistry Society, vol. 104, 1982, pp. 6139-6140.

* cited by examiner

METHOD FOR MEASURING METAL ION PERMEABILITY OF POLYMER FILM AND DEVICE FOR MEASURING METAL ION PERMEABILITY OF POLYMER FILM

CROSS-REFERENCE TO RELATED APPLICATION

This application is a 35 U.S.C. § 371 National Phase Entry Application from PCT/KR2016/001021, filed on Jan. 29,2016, and designating the United States, which claims priority under 35 U.S.C § 119 Korean Patent Application No. 10-2015-0014332 filed on Jan. 29, 2015 with the Korean Intellectual Property Office, the disclosures of which are herein incorporated by reference in their entirety.

TECHNICAL FIELD OF THE INVENTION

The present invention relates to a method for measuring metal ion permeability of a polymer film and a device for measuring metal ion permeability of a polymer film, more specifically, to a method for measuring metal ion permeability of a polymer film and a device for measuring metal ion permeability of a polymer film that can more easily and correctly measure metal ion permeability of a polymer film used in a semiconductor device, etc., and can reduce the time required for measuring, and improve efficiency.

BACKGROUND OF THE INVENTION

Metal ion permeability of a polymer film used in a semiconductor device or a display device is an important factor for securing the reliability of the material used or final products. However, a method capable of directly measuring metal ion permeability of a polymer film is not widely known, and according to previously known measurement methods, a complicated multistage process should be conducted, and the resulting measurement reliability of metal ion permeability of a polymer film is not so high.

For example, previously, a method of introducing a polymer film to be measured into a metal ion solution and heating, and then, calculating the weight of metal ions adsorbed to the polymer film was used; however, it was difficult to consider the obtained measurement result as metal ion permeability. And, as another measurement method previously known, a method of diffusing a copper precursor into a wafer, and then, combining a polymer film to be measured on the wafer to re-diffuse the copper precursor, and quantifying the amount of copper ions contained in the polymer film is known. However, according to this method, the pretreatment process and quantification process are complicated, and an excessive amount of toxic material such as hydrofluoric acid, etc. should be used.

(Patent Document 1) Korean Registered Patent No. 1311661

SUMMARY OF THE INVENTION

It is an object of the present invention to provide a method for measuring metal ion permeability of a polymer film that can more easily and correctly measure metal ion permeability of a polymer film used in a semiconductor device, etc., and can reduce a time required for measuring and thus has improved efficiency.

It is another object of the present invention to provide a device for measuring metal ion permeability of a polymer film that can more easily and correctly measure metal ion permeability of a polymer film used in a semiconductor device, etc., and can reduce a time required for measuring and thus has improved efficiency.

A method for measuring metal ion permeability of a polymer film, comprising the steps of: applying a voltage to the polymer film at a temperature of 5° C. to 250° C., while one side of the polymer film is brought into contact with an electrolyte comprising metal ions, an organic solvent and an aqueous solvent; and measuring the change rate of resistance or change rate of current of the polymer film according to time, after the voltage is applied, is provided herein.

The step of applying a voltage to the polymer film at a temperature of 5° C. to 250° C., while one side of the polymer film is brought into contact with an electrolyte comprising metal ions, an organic solvent and an aqueous solvent, may comprise a step of applying a voltage to a first electrode that is in contact with the other side of the polymer film and to a second electrode that opposes the first electrode and is in contact with the electrolyte.

The step of applying a voltage to the polymer film at a temperature of 5° C. to 250° C., while one side of the polymer film is brought into contact with an electrolyte comprising metal ions, an organic solvent and an aqueous solvent, may be progressed under a pressure of 1 atm to 5 atm.

The step of applying a voltage to the polymer film may be progressed at a temperature of 100° C. to 200° C.

The boiling point of the organic solvent included in the electrolyte may be higher than the temperature of the step of applying a voltage to the polymer film.

The organic solvent included in the electrolyte may comprise a sulfoxide organic solvent. The sulfoxide organic solvent may comprise dialkyl sulfoxide having a carbon number of 1 to 3.

The electrolyte may comprise 1 to 500 parts by weight of the organic solvent, based on 100 parts by weight of the aqueous solvent.

The electrolyte may comprise 0.1 ppmw to 2,000 ppmw of the metal ions.

The metal ions may include one or more metal ions selected from the group consisting of copper, gold, platinum, silver, iron, mercury, potassium, calcium, sodium, aluminum, nickel and chromium.

The step of measuring the change rate of resistance or change rate of current of the polymer film according to time, after the voltage is applied, may comprise a step of measuring a time until a first time (T) at which the change rate of current or resistance according to time is constantly maintained, after the voltage is applied.

The first time at which the change rate of current or resistance according to time is constantly maintained, may be the first time of a time interval in which the change rate of current or the change rate of resistance according to time is included in a range within 25% of a mean value of the change rate of current or the change rate of resistance according to time, or the first time at which the change ratio of the differential value of change of current or resistance according to time becomes 0, after passing an inflection point of change of current or resistance according to time.

The metal ion permeability of the polymer film may be defined as a average rate of change of current or the change rate of resistance according to time, after the first time (T).

The time until the first time (T) at which the change rate of current or resistance according time may be constantly maintained, after the voltage is applied, is 8 hours or less.

The time until the first time (T) at which the change rate of current or resistance according time is constantly maintained, after the voltage is applied, may be measured at a temperature of 110° C., a pressure of 1.4 atm and an applied voltage of 10V.

And, a device for measuring metal ion permeability of a polymer film, comprising a first electrode and a second electrode opposing each other; a polymer film mounting part that is installed in such a way that one side of the first electrode is in contact with a polymer resin film; an electrolyte compartment that is positioned between the second electrode and the polymer film mounting part, and includes an electrolyte comprising metal ions, an organic solvent and an aqueous solvent inside; a chamber including an internal space in which the first electrode, second electrode, electrolyte compartment and polymer film mounting part are positioned; a voltage applying part that is connected with the first electrode and the second electrode, and applies a voltage; and a electrical signal measuring part that measures resistance change or current change of the polymer film mounted on the polymer film mounting part, is also provided herein.

The electrical signal measuring part is a device that measures the change rate of resistance or change rate of current according to time of the polymer film mounted on the polymer film mounting part, after applying voltages to the first electrode and the second electrode using the voltage applying part.

The polymer film mounting part may further comprise a fixing tool that closely contacts the first electrode, the polymer film mounted on the polymer film mounting part, and the electrolyte compartment with one another, and fixes them.

The chamber may further comprise a temperature control part and a humidity control part.

And, a device for measuring metal ion permeability of a polymer film, for use in the above described method for measuring metal ion permeability of a polymer film, is also provided herein.

According to the present invention, a method for measuring metal ion permeability of a polymer film and a device for measuring metal ion permeability of a polymer film that can more easily and correctly measure metal ion permeability of a polymer film used in a semiconductor device, etc., and reduce a time required for measuring and thus have improved efficiency can be provided.

DETAILED DESCRIPTION OF THE INVENTION

Hereinafter, a method for measuring metal ion permeability of a polymer film and a device for measuring metal ion permeability of a polymer film according to specific embodiments of the present invention will be explained in more detail.

According to one embodiment of the present invention, a method for measuring metal ion permeability of a polymer film, comprising the steps of: applying a voltage to the polymer film at a temperature of 5° C. to 250° C., while one side of the polymer film is brought into contact with an electrolyte comprising metal ions, an organic solvent and an aqueous solvent; and measuring the change rate of resistance or change rate of current of the polymer film according to time, after the voltage is applied, is provided.

It is known that, metal impurities in a semiconductor device or display device, etc. have a fatal influence on the physical and electrical properties of the electrical electronic device, and thus, significantly reduce manufacturing reliability and yield, etc. Specifically, metal or metal ions diffuse into a device such as a semiconductor substrate, etc. at high temperature and is positioned at a deep level in a silicon forbidden bandgap, thus acting as a trap center that causes production and recombination of a few carriers, thereby decreasing the lifespan of a few carriers, increasing leakage current of p-n junctions, and decreasing the breakdown voltage of oxides.

Since parts of polymer films used in a semiconductor device or display device, etc., for example, a die bonding film, a solder resist, a bonding sheet for a substrate, an insulation film, etc. have insulation properties, it is not easy to measure metal permeability or metal ion permeability of the polymer resin film, or evaluate related performances.

Thus, the present inventors confirmed through experiments that by applying a voltage while a polymer film used in a semiconductor device, etc. is brought into contact with an electrolyte comprising metal ions, an organic solvent and an aqueous solvent, and after applying the voltage, measuring the change of resistance or change of current of the polymer film, metal ion permeability of the polymer film to be measured can be more correctly and easily measured, and completed the present invention.

Specifically, the method for measuring metal ion permeability of a polymer film may comprise a step of applying a voltage to the polymer film at a temperature of 5° C. to 250° C., while one side of the polymer film is brought into contact with an electrolyte comprising metal ions, an organic solvent and an aqueous solvent.

The temperature in the step of applying a voltage to the polymer film while one side of the polymer film is brought into contact with an electrolyte comprising metal ions, an organic solvent and an aqueous solvent, may be 5° C. to 250° C., or 15° C. to 200° C., or 40° C. to 200° C., or 70° C. to 200° C., or 100° C. to 200° C.

In the above explained state, if the temperature of the step of applying a voltage to the polymer film is too low, the transfer rate metal ions may become too low, thus prolonging the measurement time, and reproducibility of the transfer speed of metal ions may be insufficient, thus rendering it difficult to measure metal ion permeability or degrading the reliability of measurement result. And, in the above explained state, if the temperature of the step of applying a voltage to the polymer film is too high, the pressure of any one side of both sides of the polymer film may become too high, thus damaging the polymer film, or the transfer rate of metal ions may become excessively high, thus rendering it difficult to measure metal ion permeability or degrading the reliability of measurement result.

Meanwhile, the step of applying a voltage to the polymer film while one side is brought into contact with an electrolyte comprising metal ions, an organic solvent and an aqueous solvent, and the step of applying a voltage to the polymer film at a temperature of 5° C. to 250° C., or 15° C. to 200° C., or 40° C. to 200° C., or 70° C. to 200° C., or 100° C. to 200° C. may be carried out in a closed-type chamber.

In the method for measuring metal ion permeability of a polymer film, in order to easily control the above explained temperature condition and pressure condition and maintain the controlled state, a voltage may be applied while the polymer film is positioned in a closed-type chamber.

Here, the pressure inside the chamber may be 1 atm to 5 atm. Thus, the step of applying a voltage to a polymer film at a temperature of 5° C. to 250° C. while one side of the polymer film is brought into contact with an electrolyte comprising metal ions, an organic solvent and an aqueous solvent, may be progressed under a pressure of 1 atm to 5 atm.

And, the electrolyte may comprise metal ions, an organic solvent and an aqueous solvent.

Specifically, the electrolyte may comprise 1 to 500 parts by weight, or 5 to 300 parts by weight, or 10 to 150 part by weight of the organic solvent, based on 100 parts by weight of the aqueous solvent.

In the electrolyte, if the content of the organic solvent is excessively decreased to less than 1 part by weight, based on 100 parts by weight of the aqueous solvent, due to decrease in the penetration speed of metal ions and the resulting increase in the measuring time of metal ion permeability, in case a voltage of 0.1 V to 10.0 V is applied in a measuring device, the first time at which the change of current or resistance according to time becomes constant after the change of current or resistance according to time occurs may be increased to become greater than 10 hours, and thus, measuring efficiency may be decreased.

And, if the content of the organic solvent is excessively increased to greater than 500 parts by weight, based on 100 parts by weight of the aqueous solvent, the polymer film may be excessively swollen by the organic solvent and thus may be damaged, and the penetration time of metal ions may become too short, thus rendering it difficult to reproducibly measure the metal ion permeability of the polymer film itself.

The boiling point of the organic solvent included in the electrolyte may be higher than the temperature of the step of applying a voltage to the polymer film. More specifically, the boiling point of the organic solvent included in the electrolyte may be 10° C. to 200° C., or 50° C. to 100° C. higher than the temperature of the step of applying a voltage to the polymer film.

If the boiling point of the organic solvent included in the electrolyte is higher than the temperature of the step of applying a voltage to the polymer film by less than 10° C., during warming using a chamber, the organic solvent may be volatilized.

And, if the boiling point of the organic solvent included in the electrolyte is higher than the temperature of the step of applying a voltage to the polymer film by greater than 200° C., as the warming temperature using a chamber increases, the transfer rate of metal ions increases, thus generating excessive pressure inside a compartment, and thus, there is a concern about damage of the polymer film.

More specifically, the boiling point of the organics solvent included in the electrolyte may be 100° C. to 200° C., or 150° C. to 200° C., or 170° C. to 200° C., and the temperature of the step of applying a voltage to the polymer film may be 100° C. to 200° C., or 100° C. to 150° C., or 100° C. to 130° C.

The organics solvent included in the electrolyte may include sulfoxide organic solvents. The sulfoxide organic solvents has a moiety including a sulfinyl (—SO—) group in the molecular structure, and aliphatic, alicyclic, or aromatic hydrocarbon functional groups, respectively independently substituted or unsubstituted, may be bonded to both ends of the sulfinyl group.

The term "substituted or unsubstituted" means to include the functional groups further substituted with specific substituents, as well as each functional group itself. As used herein, unless otherwise defined, examples of the substituents that can be further substituted may include halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, siloxy, or "polar functional groups including oxygen, nitrogen, phosphorus, sulfur, silicon or boron" as explained above, etc.

More specifically, the sulfoxide organic solvent may include dialkyl sulfoxide having a carbon number of 1 to 3. The dialkyl sulfoxide having a carbon number of 1 to 3 may be a compound in which unsubstituted aliphatic hydrocarbon functional groups, for example, C1-3 alkyl groups, are respectively bonded to both ends of a sulfinyl group. Preferable example of the dialkyl sulfoxide having a carbon number of 1 to 3 may include dimethyl sulfoxide.

As such, the sulfoxide organic solvent that is used as the organic solvent included in the electrolyte has very high polarity and thus may have a high miscibility with the aqueous solvent, and may improve the transfer rate of metal ions in the electrolyte, thus remarkably reducing the measurement time of metal ion permeability.

And, the sulfoxide organic solvent that is used as the organic solvent included in the electrolyte has weak toxicity compared to the previously used N-methypyrrolidone (NMP), and thus, is favorable in terms of pro-environmental aspects.

Besides, as the organic solvent, one kind or two or more kinds of common organic solvents known to be usable as an electrolyte may be mixed and used, and examples of the organic solvents may include alcohols such as methanol, ethanol, propanol, iso-propanol, butanol, or pentanol, acids such as acetic acid, nitric acid or hydrochloric acid, etc., n-methyl pyrrolidone (NMP), acetone, dimethylformamide, tetrahydrofurane (THF), dioxane, dimethylacetamide, polyethyleneglycol (PEG), xylene, toluene, chloroform, etc., but are not limited thereto.

As the aqueous solvent, water may be used.

The metal ion may include one or more ions of metal selected from the group consisting of copper, gold, platinum, silver, iron, mercury, potassium, calcium, sodium, aluminum, nickel and chromium.

And, although the concentration of the electrolyte comprising the metal ions is not significantly limited, in order to facilitate the operation of the device for measuring metal ion permeability of a polymer film and more clearly measure the metal ion permeability, it is preferable that the concentration of metal ions is 0.1 ppmw to 2,000 ppmw.

Although the method of including the metal ions in the electrolyte is not significantly limited, for example, a method of mixing metal salts containing the metal ions with an aqueous solvent and an organic solvent, etc. may be used.

Thus, the electrolyte may further comprise anions. The anion means a negatively (−) charged ion, and it may combine with the metal ions and exist in the form of a metal salt, or may be separated from the metal ions and exist in the form of a separate anion. That is, as explained above, in case a method of mixing metal salts containing metal ions with an aqueous solvent and an organic solvent is used, anions derived from the metal salt may remain in the electrolyte.

The examples of the anions are not significantly limited, and for example, may include sulfate ion ($SO_4^{2-}$), nitrate ion ($NO_3^-$), perchlorate ion ($ClO_4^-$), halogenated ion ($F^-$, $Br^-$, $Cl^-$, $I^-$), hydroxide ion ($OH^-$), acetate ion ($CH_3COO^-$), etc., and preferably, sulfate ion ($SO_4^{2-}$).

In case the sulfate ion ($SO_4^{2-}$) is contained in the electrolyte, due to its structural similarity to the above explained sulfoxide organic solvents used as an organic solvent, miscibility in the electrolyte may be further improved, and thus, mobility of metal ions may become fast, thus remarkably reducing the measurement time of metal ion permeability.

The concentration of the anions may be identical to the above explained concentration of metal ions, or it may be higher or lower than the concentration of metal ions so as to charge balance with the quantity of electric charge of metal ions. And, the anion may exist in the form of a separate anion in the electrolyte, or it may react with an aqueous solvent and exist in the form of a hydrate or acid.

In the method for measuring metal ion permeability according to one embodiment, the step of applying a voltage to the polymer film at a temperature of 5° C. to 250° C., while one side of the polymer film is brought into contact with an electrolyte comprising metal ions, an organic solvent and an aqueous solvent, may comprise a step of applying a voltage to a first electrode that is in contact with the other side of the polymer film and to a second electrode that opposes the first electrode and is in contact with the electrolyte.

That is, only one side of the polymer film may contact with the electrolyte, and the opposite side to the one side may not contact with the electrolyte but contact with a first electrode. The opposite side means another side that is parallel to one side contacting with the electrolyte. As such, by contacting one side of the polymer film with the electrolyte and directly contacting the opposite side with the second electrode, the polymer film may be supported to realize structural stability.

The step of applying a voltage while one side of the polymer film is brought into contact with an electrolyte comprising metal ions, an organic solvent and an aqueous solvent, may comprise a step of applying a voltage to a first electrode that is in contact with the other side of the polymer film and to a second electrode that opposes the first electrode and is in contact with the electrolyte.

Here, the electrolyte may comprise 0.1 ppmw to 2,000 ppmw of metal ions, and for example, as the electrolyte, a first solution comprising copper ions or a second solution comprising sodium ions may be used, and preferably, a first solution comprising copper ions may be used.

The first solution containing copper ions may comprise copper ions, an organic solvent and an aqueous solvent, and the second solution containing sodium ions may comprise sodium ions, an organic solvent and an aqueous solvent. The above explained applies to the organic solvent and the aqueous solvent.

And, the concentration of copper ions in the first solution may be 0.1 ppmw to 2,000 ppmw, and the concentration of sodium ions in the second solution may be 0.1 ppmw to 2,000 ppmw.

And, the method for measuring metal ion permeability may comprise a step of measuring the change rate of resistance or change rate of current of the polymer film according to time, after the voltage is applied.

Specifically, the metal ion permeability of a polymer film may be determined as a time until the first time (T) at which the change rate of current or resistance according to time is constantly maintained, from the time at which a predetermined voltage (for example, 0.1 V to 10.0 V) is applied.

The meaning of the description "the change rate of current or resistance according to time is constantly maintained" includes a case wherein, in the corresponding time interval, the change rate of current or resistance according to time is included in a range within 25% of the mean value of the change rate of current or the change rate of resistance according to time, and a case wherein the change ratio of instantaneous rate of change of current or resistance according to time (or the change ratio of the differential value of change of current or resistance according to time) becomes 0, etc.

The first time (T) at which the change rate of current or resistance according time is constantly maintained means a first time at which the change of current or resistance according to time becomes constant, after the change of current or resistance according time occurs, and it may appear after passing an inflection point of the change of current or resistance according to time.

The first time (T) may be determined as a first time at which the change ratio of the instantaneous rate of change of current or resistance according to time (or the change ratio of the differential value of current or resistance change according to time) becomes 0, or as a first time in a time interval in which the change rate of current or resistance according to time is included in a range within 25% of the mean value of the change rate of current or the change rate of resistance according to time.

For the determination of the first time, various methods can be used without specific limitations, and for example, it may be determined by calculating the average change rate of current or resistance according to time in a corresponding time interval, and extrapolating a time at which the average change rate value appears, after passing an inflection point of current or resistance change according to time.

Although the range of change rate of current or change rate of resistance that can be measured by the measurement method of metal ion permeability of a polymer film of the above embodiment is not significantly limited, for example, in case a voltage of 0.1 V to 10.0 V is applied, the first time at which the change of current or resistance becomes constant, after change of current or resistance according to time occurs, may be 8 hours or less, or 0.5 hours to 8 hours.

More specifically, a time until the first time (T) at which the change rate of current or resistance according to time is constantly maintained after the voltage is applied, may be measured at a temperature of 110° C., a pressure of 1.4 atm and an applied voltage of 10V.

Meanwhile, the metal ion permeability may be represented by the change rate of current or voltage according to time, and specifically, it may be the average rate of change of current or voltage according to time, after the first time (T), and for example, it may be A/10 seconds, A/1 minutes, A/1 hours, A/10 hours, Ω/10 seconds, Ω/1 minutes, Ω/1 hours, Ω/10 hours, etc.

In the measurement method of metal ion permeability of a polymer film of the above embodiment, the measuring device of the change rate of current or change rate of voltage is not significantly limited in terms of its kind or structure, any device capable of measuring the change of current or change of voltage occurred in a polymer film to be measured, after applying a voltage, may be used without significant limitations, and for example, devices such as a potentiostat, etc. may be used.

The size of the voltage applied to the polymer film while one side is brought into contact with an electrolyte comprising metal ions, an organic solvent and an aqueous solvent, may be selected within a range of 0.001 V to 100 V, considering the kind of the polymer film or the measured value of current change or resistance change.

Meanwhile, although the kind of polymer films of which metal ion permeability can be measured by the above described method for measuring metal ion permeability of a polymer film is not significantly limited, a polymer film having an insulation property may be the main subject of the measurement of metal ion permeability. Specifically, the polymer films for which the above described method for measuring metal ion permeability of a polymer film can be applied, may include a die bonding film, a solder resist, a bonding sheet for a substrate, an insulation film, etc.

Figure 1:
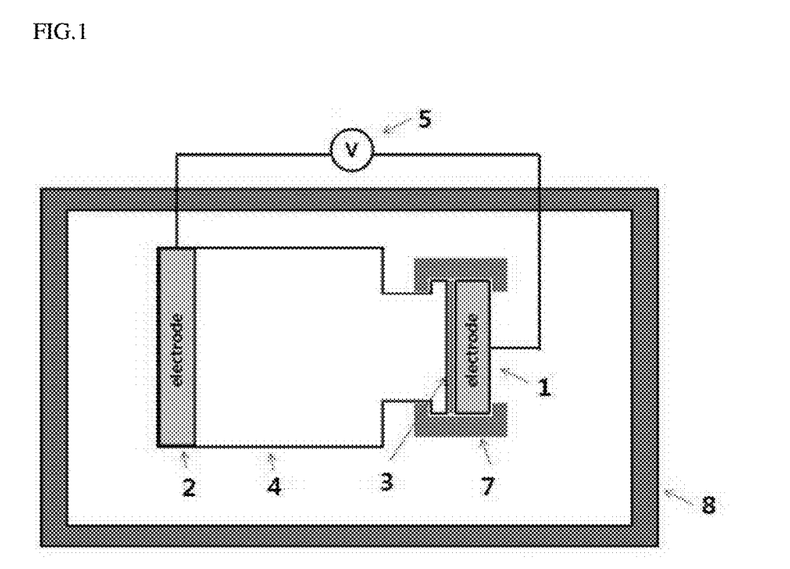
FIG. 1 schematically shows one example of a device for measuring metal ion permeability of a polymer film according to Example of the present invention.

Meanwhile, according to one embodiment of the present invention, a device for measuring metal ion permeability of a polymer film, comprising: a first electrode(1) and a second electrode(2) opposing each other; a polymer film mounting part(3) that is installed in such a way that one side of the first electrode is in contact with a polymer resin film; an electrolyte compartment(4) that is positioned between the second electrode and the polymer film mounting part, and includes an electrolyte comprising metal ions, an organic solvent and an aqueous solvent inside; a chamber(8) including an internal space in which the first electrode, second electrode, electrolyte compartment and polymer film mounting part are positioned; a voltage applying part(5) that is connected with the first electrode and the second electrode, and applies a voltage; and a electrical signal measuring part(6) that measures resistance change or current change of the polymer film mounted on the polymer film mounting part, is provided.

The present inventors confirmed through experiments that by applying a voltage while both sides of a polymer film used in a semiconductor device, etc. are brought into contact with a predetermined electrolytes, and after applying the voltage, measuring the change of resistance or change of current of the polymer film, metal ion permeability of the polymer film to be measured can be more correctly and easily measured, and based thereon, invented a device for measuring metal ion permeability of a polymer film and completed the present invention.

Specifically, in the device for measuring metal ion permeability of a polymer film of the above embodiment, if voltages are applied to the first electrode and second electrode, metal ions positioned in the electrolyte compartment (4) including an electrolyte comprising metal ions, an organic solvent and an aqueous solvent inside moves by current, and thus, when the metal ions penetrate the polymer film positioned on the polymer film mounting part, current flows and resistance becomes low, thus generating an electrical signal.

Thus, in the above embodiment, the metal ion permeability of a polymer film can be measured as a rate of change of resistance or a rate of change of current according to time, said change beginning to appear when the metal ions begin to penetrate the polymer film, after a voltage is applied to the polymer film to be measured.

Specifically, the metal ion permeability of a polymer film can be determined as a time until the first time (T) at which the change rate of current or resistance according to time is constantly maintained, from the time at which a predetermined voltage (for example, 0.1 V to 10.0 V) is applied.

The meaning of the description "the change rate of current or resistance according to time is constantly maintained" includes a case wherein, in the corresponding time interval, the change rate of current or resistance according to time is included in a range within 25% of the mean value of the change rate of current or the change rate of resistance according to time, and a case wherein the change ratio of instantaneous rate of change of current or resistance according to time (or the change ratio of the differential value of change of current or resistance according to time) becomes 0, etc.

The first time (T) at which the change rate of current or resistance according time is constantly maintained means a first time at which the change of current or resistance according to time becomes constant, after the change of current or resistance according time occurs, and it may appear after passing an inflection point of the change of current or resistance according time.

The first time (T) may be determined as a first time at which the change ratio of the instantaneous rate of change of current or resistance according to time (or the change ratio of the differential value of current of resistance change according to time) becomes 0, or as a first time in a time interval in which the change rate of current or resistance according to time is included in a range within 25% of the mean value of the change rate of current or the change rate of resistance according to time.

For the determination of the first time, various methods can be used without specific limitations, and for example, it may be determined by calculating the average change rate of current or resistance according to time in the corresponding time interval, and extrapolating a time at which the average change rate value appears, after passing an inflection point of current or resistance change according to time.

Although the range of change rate of current or change rate of resistance that can be measured by the measurement device of metal ion permeability of a polymer film of the above embodiment is not significantly limited, for example, in case a voltage of 0.1 V to 10.0 V is applied to the measurement device, the first time at which the change of current or resistance becomes constant, after change of current or resistance according to time appears, may be 8 hours or less, or 0.5 hours to 8 hours.

Meanwhile, the metal ion permeability may be represented by the change rate of current or resistance according time, and specifically, it may be the average rate of change of current of resistance according to time, after the first time (T), and for example, it may be A/10 seconds, A/1 minutes, A/1 hour, A/10 hours, $\Omega$/10 seconds, $\Omega$/1 minute, $\Omega$/1 hour, $\Omega$/10 hours, etc.

More specifically, if a polymer film of which metal ion permeability is to be measured is positioned on the polymer film mounting part(3), the electrolyte comprising metal ions, an organic solvent and an aqueous solvent in the electrolyte compartment(4) contacts with one side of the polymer film. And, while one side of the polymer film contacts with the electrolyte comprising metal ions, an organic solvent and an aqueous solvent, voltages are applied to a first electrode that is in contact with the other side of the polymer film and to a second electrode that opposes the first electrode and is in contact with the electrolyte, using a voltage applying part(5) that is connected to the first electrode and second electrode and applies voltages, and thereafter, the change of resistance or change of current of the polymer film mounted on the polymer film mounting part is measured using an electrical signal measuring part(6).

Specifically, examples of the method of contacting the electrolyte with the second electrode in the electrolyte compartment is not significantly limited, and for example, a method of impregnating the second electrode with the electrolyte compartment including the electrolyte inside, or a method of contacting the electrolyte compartment with one side of the second electrode, so that a space defined by a partition wall (side wall) connecting the second electrode(2) and the polymer film mounting part(3) may become the electrolyte compartment, etc. may be used.

The size of the voltages applied to the first electrode and the second electrode is not significantly limited, and it may be selected within a range of 0.001 V to 100 V considering the kind of the polymer film or the measured value of resistance change or current change.

As explained above, the electrolyte compartment is positioned between the second electrode and the polymer film mounting part, and an electrolyte comprising metal ions, an organic solvent and an aqueous solvent may be positioned therein.

The above explained with regard to one embodiment applies to the electrolyte, metal ions, organic solvent and aqueous solvent.

As the first electrode(1) and second electrode(2), common electrodes known to be used in a secondary battery, etc. may be used, and for example, copper, aluminum lithium, platinum, gold, iron, zinc, nickel, silver, lead, carbon electrodes, ITO or PEDOT/PSS, etc. may be used.

The polymer film mounting part(3) that is installed in such a way that one side of the first electrode is in contact with a polymer resin film may be defined as a space formed between the first electrode(1) and the electrolyte compartment(4), and it may also be defined as a separate mounting device or fixing device installed in the space. For example, the polymer film mounting part(3) may be a space of a spherical shape, circular shape, or polygon of which cross section has 3 to 20 internal angles, and may comprise a glass filter or a polymer film support part of a mesh shape.

And, the polymer film mounting part(3) may further comprise a fixing tool(7) that closely contacts the electrolyte compartment and the polymer film mounted on the polymer film mounting part with one another, and fixes them. Specific shape or practical fastening method or structure of the fixing tool(7) is not significantly limited, and for example, a fixing tool(jig) of a structure that can be added to the rear side of the external protrusion part of the polymer film mounting part may be used, a hole penetrating the fixing tool and the external protrusion part of the polymer film mounting part may be connected with a screw to press, and both ends of a belt-shaped structure with a groove of an oblique angle covering the external protrusion part of the polymer film mounting part may be fixed with a screw to press.

The electrolyte compartment(4) is positioned between the second electrode(2) and the polymer film mounting part(3), and means a space defined by a partition wall (side wall) connecting the second electrode(2) and the polymer film mounting part(3)

The material of the partition wall (side wall) of the electrolyte compartment(4) is not significantly limited, and it may comprise material having high stability to electrolyte staying inside, and having stability under temperature and pressure conditions applied in the process of measuring metal ion permeability. Specifically, the partition wall (side wall) of the electrolyte compartment may include materials such as glass, Teflon, or polymer, etc., but specific examples are not limited thereto.

And, although the thickness of the partition wall of the electrolyte compartment is not significantly limited, for example, it may have a thickness of 1 mm to 500 mm.

And, although the concentration of the electrolyte comprising the metal ions is not significantly limited, in order to facilitate the operation of the device for measuring metal ion permeability of a polymer film and more clearly measure the metal ion permeability, it is preferable that electrolyte with the concentration of metal ions of 0.1 ppmw to 2,000 ppmw stays in the electrolyte compartment(4).

Specific kind or structure of the electrical signal measuring part is not significantly limited, devices capable of measuring change of resistance or change of current generated in the polymer film to be measured after applying a voltage may be used without significant limitations, and for example, devices such as a potentiostat, etc. may be used.

The voltage applying part; and the electrical signal measuring part(6) may be positioned inside or outside the chamber, and it may be installed in the chamber itself.

As the chamber, reaction chambers made of commonly known material may be used, and the shape or structure of the chamber is not significantly limited.

And, the chamber may further comprise a temperature control part and a humidity control part.

The temperature inside the chamber may be 0° C. to 400° C., and through the temperature control part installed in the chamber, the temperature in the process of measuring metal ion permeability of a polymer film may be controlled. Specific structure or kind of the temperature control part is not significantly limited, and for example, it may include devices such as a convection oven, a HAST ([Highly Accelerated Stress Test] oven or a PCT (Pressure Cooker Test) oven, etc.

In case the device for measuring metal ion permeability of a polymer film is operated to measure metal ion permeability, the temperature inside the chamber may be 5° C. to 250° C., or 15° C. to 200° C., or 40° C. to 200° C., or 70° C. to 200° C., or 100° C. to 200° C.

In case the device for measuring metal ion permeability of a polymer film is operated to measure metal ion permeability, the pressure inside the chamber may be 1 atm to 5 atm.

Meanwhile, although the kind of polymer films that can be applied for the device for measuring metal ion permeability of a polymer film is not significantly limited, polymer films having insulation property may be the main subjects of the measurement of metal ion permeability. Specifically, the polymer films that can be applied for the device for measuring metal ion permeability of a polymer film may include a die bonding film, a solder resist, a bonding sheet for a substrate, an insulation film, etc.

Meanwhile, according to still another embodiment of the present invention, a device for measuring metal ion permeability of a polymer film, for use in the method for measuring metal ion permeability of a polymer film of one embodiment, is provided.

The above explained applies to the method for measuring metal ion permeability of a polymer film and the operation device thereof.

Hereinafter, the present disclosure will be explained in detail with reference to the following examples. However, these examples are only to illustrate the inventive concept, and the scope of the inventive concept is not limited thereto.

PREPARATION EXAMPLES 1 to 3

Preparation of an Adhesive Film Having Insulation Property (1) Preparation of a Solution of a Resin Composition Phenol resin, epoxy resin, acrylic resin, a cure accelerator, a coupling agent, and a filler were dissolved in methylethylketone with the contents described in the following Table 1, to obtain a solution of an adhesive resin composition for semiconductor (solid content 20 wt %).

(2) Preparation of an Adhesive Film

The above prepared solution of an adhesive resin composition for semiconductor was coated on a polyethylene terephthalate film (thickness 38 μm), and then, dried at 130° C. for 3 minutes to obtain an adhesive film with a thickness of 20 μm. The glass transition temperature (TMA measurement) and modulus (DMA measurement) of each adhesive film of Preparation Examples 1 to 3 were measured, and the results are shown in the following Table 2.

TABLE 1

Composition of a solution of a resin composition [unit: g]

| Components | | Preparation Example 1 | Preparation Example 2 | Preparation Example 3 |
|---|---|---|---|---|
| Phenol resin | KPH-F2001 | 50 | — | 50 |
|  | KH-6021 | — | 50 | — |
| Epoxy resin | EOCN-104S | 100 | 100 | — |
|  | HP-7200 | — | — | 100 |
| Acrylic resin | KG-3037 | 500 | 500 | 500 |
| Cure accelerator | 2P4MHZ | 0.5 | 0.5 | 0.5 |
| Coupling agent | KBM-403 | 2 | 2 | 2 |
| Filler | RY-50 | 90 | 90 | 90 |

KPH-F2001: phenol novolac resin (Kolon Chemical Co., Ltd., hydroxyl equivalent: 106 g/eq, softening point: 88° C.)
KH-6021: bisphenolA novolac phenol resin (DIC Corp, hydroxyl equivalent: 118 g/eq, softening point: 133° C.)
EOCN-104S: cresol novolac phenol resin (Nippon Kayaku, epoxy equivalent: 214 g/eq, softening point: 92° C.)
HP-7200: DCPD-based novolac phenol resin (DIC Corp, epoxy equivalent: 257 g/eq, softening point: 62° C.)
KG-3037: acrylate-based resin (glycidyl methacrylate-based repeat units 13 wt %, glass transition temperature: 20° C., Mw 800,000)
2P4MHZ: 2-phenyl-4-methyl-5-dihydroxymethyl imidazole (Shikoky Chemical Corp.)
KBM-403: gamma-glycidoxy propyl trimethoxy silane (Shin-etsu Chemical Co., Ltd.)
RY-50: spherical silica (Evonik, average particle diameter 40 nm)

TABLE 2

Properties of adhesive films

|  | Preparation Example 1 | Preparation Example 2 | Preparation Example 3 |
|---|---|---|---|
| Glass transition temperature (° C.) | 180 | 170 | 165 |
| Modulus (MPa) | 5 | 4 | 5 |

EXAMPLES 1 to 9

A Device For Measuring Metal Ion Permeability of a Polymer Film And Measurement of Metal Ion Permeability of a Polymer Film

EXAMPLE 1

(1) Manufacture of a Device for Measuring Metal Ion Permeability of a Polymer Film As shown in FIG. 1, a device for measuring metal ion permeability of a polymer film, comprising a first electrode and a second electrode opposing each other; a polymer film mounting part that is installed in such a way that one side of the first electrode is in contact with a polymer resin film; an electrolyte compartment that is positioned between the second electrode and the polymer film mounting part, and includes an electrolyte comprising metal ions, an organic solvent and an aqueous solvent inside; a chamber including an internal space in which the first electrode, second electrode, electrolyte compartment and polymer film mounting part are positioned; a voltage applying part that is connected with the first electrode and the second electrode, and applies a voltage; and an electrical signal measuring part that measures resistance change or current change of the polymer film mounted on the polymer film mounting part, was manufactured.

(2) Measurement of Metal Ion Permeability of a Polymer Film

On the above manufactured device for measuring metal ion permeability of a polymer film, the adhesive film with a thickness of 20 μm obtained in Preparation Example 1 was mounted, and at a temperature of 110° C. and a pressure of 1.4 atm, as shown in FIG. 1, in the electrolyte compartment, water ($H_2O$) and dimethyl sulfoxide (DMSO) were filled respectively at each weight ratio such that the concentration of copper sulfate ($Cu_2SO_4$) became 1000 ppmw, and then, while applying a voltage of 10 V, the first time at which the change of current or resistance according to time became constant, after the change of current or resistance according to time occurred, was judged as the end time of measurement. And, a time (T) until the measurement end time from the time at which the voltage is applied, was calculated, and measurement efficiency of metal ion permeability was evaluated according the following standard.

Excellent: The T value is measured within 8 hours
Faulty: The T value is measured to be greater than 8 hours EXAMPLES 2 to 9

A device for measuring metal ion permeability of a polymefilm was manufactured and metal ion permeability was measured by the same method as Example 1, except that the kind of an adhesive film, measurement temperature, measurement pressure, and the weight ratio of $H_2O$:DMSO of the electrolyte varied as described in Table 3.

TABLE 3

Measurement conditions and results of metal ion permeability of Examples 1 to 9

|  | Adhesive film | Measurement Temperature (° C.) | Measurement Pressure (atm) | Ratio of $H_2O$:DMSO | Measurement end time(H) | Efficiency Evaluation result |
|---|---|---|---|---|---|---|
| Example 1 | Preparation Example 1 | 110 | 1.4 | 1:1 | 2.7 | Excellent |
| Example 2 | Preparation Example 2 |  |  |  | 2.1 | Excellent |
| Example 3 | Preparation Example 3 |  |  |  | 3.3 | Excellent |

TABLE 3-continued

Measurement conditions and results of metal ion permeability of Examples 1 to 9

| | Adhesive film | Measurement Temperature (° C.) | Measurement Pressure (atm) | Ratio of H₂0:DMSO | Measurement end time(H) | Efficiency Evaluation result |
|---|---|---|---|---|---|---|
| Example 4 | Preparation Example 1 | | | 7:3 | 3.4 | Excellent |
| Example 5 | Preparation Example 2 | | | | 3.0 | Excellent |
| Example 6 | Preparation Example 3 | | | | 3.7 | Excellent |
| Example 7 | Preparation Example 1 | | | 9:1 | 4.3 | Excellent |
| Example 8 | Preparation Example 2 | | | | 3.8 | Excellent |
| Example 9 | Preparation Example 3 | | | | 5.0 | Excellent |

As shown in Table 3, in the case of Examples, by evaluating the reliability of an adhesive film by metal ion permeability, it could be rapidly measured within 8 hours under various conditions, and the reproducibility of the measurement results appeared excellent.

COMPARATIVE EXAMPLES 1 to 19

Measurement Of Metal Ion Permeability of Polymer Film

COMPARATIVE EXAMPLE 1

On a flexible copper circuit board, the adhesive film obtained in Preparation Example 1 was mounted such that the comb-shaped electrodes cross each other, and while applying voltage of 3V to both electrodes under the conditions of 110° C., 85% RH, insulation resistance value between the electrodes according to time was measured, and the moment at which the insulation resistance value between the electrodes became lower than $1\times10^5 \Omega$ was judged as an end time of measurement. And, a time (T') until the end time of measurement from the time at which voltage was applied was calculated, and measurement efficiency of metal ion permeability was evaluated according to the following standards.

Excellent: The T' value is measured to be within 8 hours
Faulty: The T' value is measured to be greater than 8 hours COMPARATIVE EXAMPLES 2 to 18

Metal ion permeability was measured by the same method as Comparative Example 1, except that the kind of adhesive films, measurement temperature, and applied voltage varied as shown in the following Table 4.

TABLE 4

Measurement conditions and results of metal ion permeability of Comparative Examples 1 to 18

| | Adhesive film | Measurement Temperature (° C.) | Applied Voltage (V) | Measurement End time (H) | Efficiency Evaluation Result |
|---|---|---|---|---|---|
| Comparative Example 1 | Preparation Example 1 | 110 | 3 | 345 | Faulty |
| Comparative Example 2 | Preparation Example 2 | | 3 | 285 | Faulty |
| Comparative Example 3 | Preparation Example 3 | | 3 | 393 | Faulty |
| Comparative Example 4 | Preparation Example 1 | | 10 | 211 | Faulty |
| Comparative Example 5 | Preparation Example 2 | | 10 | 183 | Faulty |
| Comparative Example 6 | Preparation Example 3 | | 10 | 244 | Faulty |
| Comparative Example 7 | Preparation Example 1 | | 20 | 155 | Faulty |
| Comparative Example 8 | Preparation Example 2 | | 20 | 127 | Faulty |
| Comparative Example 9 | Preparation Example 3 | | 20 | 171 | Faulty |
| Comparative Example 10 | Preparation Example 1 | 130 | 3 | 247 | Faulty |
| Comparative Example 11 | Preparation Example 2 | | 3 | 210 | Faulty |
| Comparative Example 12 | Preparation Example 3 | | 3 | 280 | Faulty |
| Comparative Example 13 | Preparation Example 1 | | 10 | 130 | Faulty |
| Comparative Example 14 | Preparation Example 2 | | 10 | 115 | Faulty |
| Comparative Example 15 | Preparation Example 3 | | 10 | 145 | Faulty |
| Comparative Example 16 | Preparation Example 1 | | 20 | 95 | Faulty |
| Comparative Example 17 | Preparation Example 2 | | 20 | 83 | Faulty |
| Comparative Example 18 | Preparation Example 3 | | 20 | 105 | Faulty |

As shown in Table 4, in the case of Comparative Examples, since the reliability of an adhesive film was evaluated by a high temperature, high humidity HAST method, even if conditions were modified, the end time of measurement was significantly prolonged such as greater than 50 hours, etc., and thus, it could be confirmed that measurement efficiency are very bad.

That is, in the case of metal ion permeation of an adhesive film according to Examples, evaluation results can be confirmed within a short time compared to the conventional reliability evaluation method of an adhesive film, and thus, measurement efficiency can be further improved, and the reproducibility of measurement results appears excellent.

COMPARATIVE EXAMPLE 19

Figure 2:
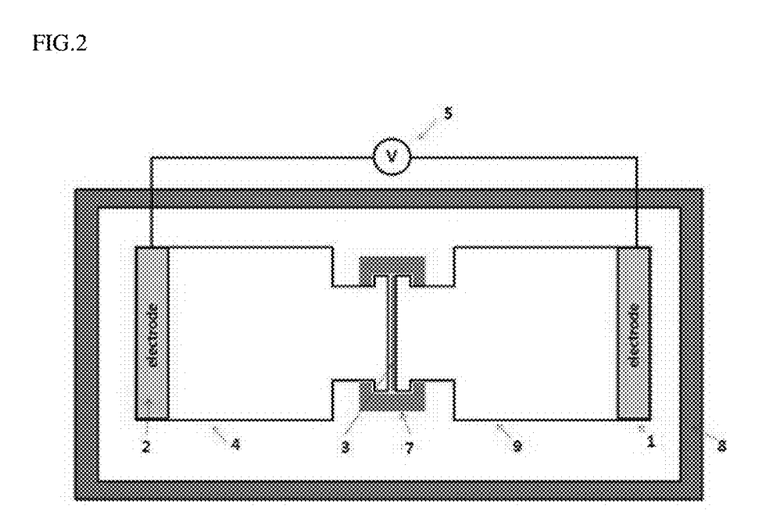
FIG. 2 schematically shows one example of a device for measuring metal ion permeability of a polymer film according to Comparative Example.
Figure 3:
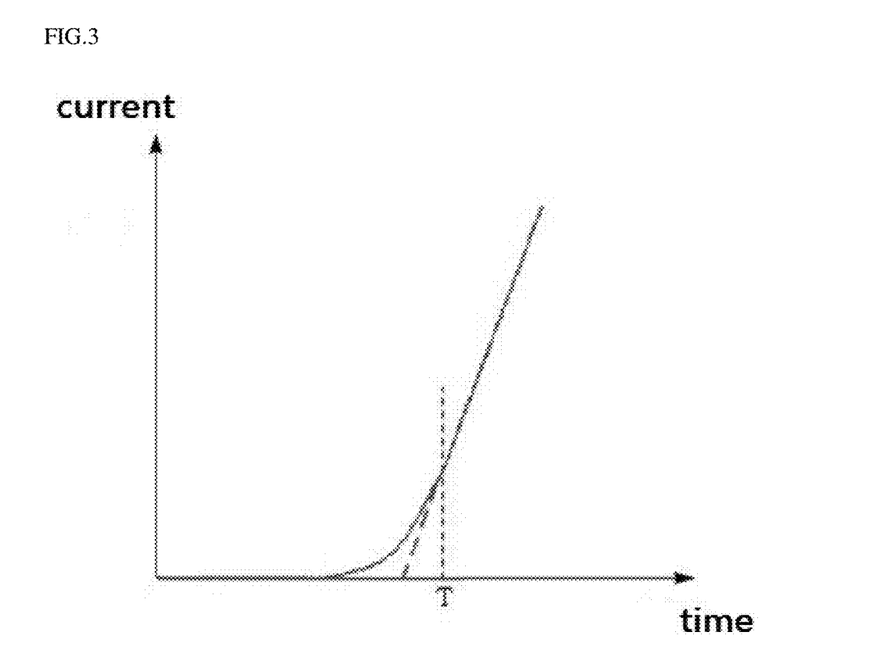
FIG. 3 is a graph showing the change of current according to time, after applying a voltage to a device for measuring metal ion permeability of a polymer film of Example.

As shown in FIG. 2, metal ion permeability was measured by the same method as Example 1, except using a device for measuring metal ion permeability of a polymer film, comprising: a first electrode and a second electrode opposing each other; a first electrolyte compartment that is in contact with the first electrode, and includes an electrolyte comprising metal ions, an organic solvent and an aqueous solvent inside; a polymer film mounting part that is positioned between the second electrode and the electrolyte compartment, and is installed in such a way that the electrolyte compartment is in contact with a polymer rein film; a second electrolyte compartment that is positioned between the second electrode and the polymer film mounting part, and includes an electrolyte comprising metal ions, an organic solvent and an aqueous solvent inside; a chamber including an internal space in which the first electrode, second electrode, electrolyte compartment and polymer film mounting part are positioned; a voltage applying part that is connected with the first electrode and the second electrode, and applies a voltage; and a electrical signal measuring part that measures resistance change or current change of the polymer film mounted on the polymer film mounting part.

In this case, as pressure imbalance of both compartments (first electrolyte compartment and second electrolyte compartment) increases due to pressure increase, the polymer film was damaged and both electrolytes (first electrolyte and second electrolyte) were mixed with each other, thus degrading the reliability of measurement.

Thus, it could be confirmed that in case a device for measuring metal ion permeability comprising two or more electrolyte compartments is used as in Comparative Example 19, if a measurement temperature is increased to 110° C. as in Examples, there is a concern about degradation of measurement reliability (for example, sudden increase in current or resistance value at the beginning of measurement, etc.) due to damage of the internal polymer film.

DESCRIPTION OF SYMBOLS

1—first electrode
2—second electrode
3—polymer film mounting part
4—electrolyte compartment
5—voltage applying part
6—electrical signal measuring part
7—fixing tool
8—chamber
9—second electrolyte compartment

What is claimed is:

1. A method for measuring metal ion permeability of a polymer film, comprising the steps of:
    applying a voltage to the polymer film at a temperature of 5° C. to 250° C. using a device, while one side of the polymer film is brought into contact with an electrolyte comprising metal ions, an organic solvent and an aqueous solvent, wherein the device comprises: a first electrode and a second electrode opposing each other; a polymer film mounting part that is installed in such a way that one side of the first electrode is in contact with a polymer resin film; an electrolyte compartment that is positioned between the second electrode and the polymer film mounting part, and includes an electrolyte comprising metal ions, an organic solvent and an aqueous solvent inside; a chamber including an internal space in which the first electrode, the second electrode, the electrolyte compartment and the polymer film mounting part are positioned; a voltage applying part that is connected with the first electrode and the second electrode, and applies a voltage; and an electrical signal measuring part that measures resistance change or current change of the polymer film mounted on the polymer film mounting part; and
    measuring using the electrical signal measuring part of the device a change rate of resistance or change rate of current of the polymer film according to time, by measuring a time until a first time (T) at which the change rate of current or the change rate of resistance according to time is constantly maintained, after the voltage is applied, thereby measuring the metal ion permeability of the polymer film as an average rate of change of current or the change rate of resistance according to time, after the first time (T).

2. The method of claim 1, wherein the step of applying the voltage to the polymer film at the temperature of 5° C. to 250° C., while the one side of the polymer film is brought into contact with the electrolyte comprising metal ions, the organic solvent and the aqueous solvent, comprises a step of applying a voltage to a first electrode that is in contact with other side of the polymer film and to a second electrode that opposes the first electrode and is in contact with the electrolyte.

3. The method of claim 1, wherein the step of applying the voltage to the polymer film at the temperature of 5° C. to 250° C., while the one side of the polymer film is brought into contact with the electrolyte comprising the metal ions, the organic solvent and the aqueous solvent, is conducted under a pressure of 1 atm to 5 atm.

4. The method of claim 1, wherein the step of applying the voltage to the polymer film is conducted at a temperature of 100° C. to 200° C.

5. The method of claim 1, wherein a boiling point of the organic solvent included in the electrolyte is higher than a temperature of the step of applying the voltage to the polymer film.

6. The method of claim 1, wherein the organic solvent included in the electrolyte comprises a sulfoxide organic solvent.

7. The method of claim 6, wherein the sulfoxide organic solvent comprises dialkyl sulfoxide having a carbon number of 1 to 3.

8. The method of claim 1, wherein the electrolyte comprises 1 to 500 parts by weight of the organic solvent, based on 100 parts by weight of the aqueous solvent.

9. The method of claim 1, wherein the electrolyte comprises 0.1 ppmw to 2,000 ppmw of the metal ions.

10. The method of claim 1, wherein the metal ions include one or more metal ions selected from the group consisting of copper, gold, platinum, silver, iron, mercury, potassium, calcium, sodium, aluminum, nickel and chromium.

11. The method of claim 1, wherein the first time at which the change rate of current or the change rate of resistance according to time is constantly maintained, is
    the first time of a time interval in which the change rate of current or the change rate of resistance according to time is included in a range within 25% of a mean value of the change rate of current or the change rate of resistance according to time, or
    the first time at which a change ratio of a differential value of change of current or change of resistance according to time becomes 0, after passing an inflection point of the change of current or the change of resistance according to time.

12. The method of claim 1, wherein the time until the first time (T) at which the change rate of current or the change rate of resistance according time is constantly maintained, after the voltage is applied, is 8 hours or less.

13. The method of claim 12, wherein the time until the first time (T) at which the change rate of current or the change rate of resistance according time is constantly maintained, after the voltage is applied, is measured at a temperature of 110° C., a pressure of 1.4atm and an applied voltage of 10V.

14. A device for measuring metal ion permeability of a polymer film, for used in the method for measuring metal ion permeability of the polymer film of claim 1.

15. A device for measuring metal ion permeability of a polymer film, comprising:
- a first electrode and a second electrode opposing each other;
- a polymer film mounting part that is installed in such a way that one side of the first electrode is in contact with a polymer resin film;
- an electrolyte compartment that is positioned between the second electrode and the polymer film mounting part, and includes an electrolyte comprising metal ions, an organic solvent and an aqueous solvent inside;
- a chamber including an internal space in which the first electrode, the second electrode, the electrolyte compartment and the polymer film mounting part are positioned;
- a voltage applying part that is connected with the first electrode and the second electrode, and applies a voltage; and
- an electrical signal measuring part that measures resistance change or current change of the polymer film mounted on the polymer film mounting part, wherein the metal ion permeability of the polymer film is defined as an average rate of change of current or the change rate of resistance according to time, after the first time (T).

16. The device of claim 15, wherein the electrical signal measuring part is a device that measures the change rate of resistance or the change rate of current according to time of the polymer film mounted on the polymer film mounting part, after applying voltages to the first electrode and the second electrode using the voltage applying part.

17. The device of claim 15, wherein the polymer film mounting part further comprises a fixing tool that closely contacts and fixes the first electrode, the polymer film mounted on the polymer film mounting part, and the electrolyte compartment with one another.

18. The device of claim 15, wherein the chamber further comprises a temperature control part and a humidity control part.

* * * * *